(12) United States Patent
Liu et al.

(10) Patent No.: US 9,388,378 B2
(45) Date of Patent: Jul. 12, 2016

(54) *CANDIDA SAKE* STRAIN FOR PRODUCING LONG CHAIN DICARBOXYLIC ACIDS

(75) Inventors: Charlie Liu, Shanghai (CN); Jinxiu Liao, Shanghai (CN); Jianglin Wang, Shanghai (CN); Haibin Qin, Shanghai (CN); Naiqiang Li, Shanghai (CN)

(73) Assignees: CATHAY R&D CENTER CO., LTD., Shanghai (CN); CATHAY INDUSTRIAL BIOTECH LTD., George Town, Grand Cayman (KY)

( * ) Notice: Subject to any disclaimer, the term of this patent is extended or adjusted under 35 U.S.C. 154(b) by 0 days.

(21) Appl. No.: 14/384,154

(22) PCT Filed: Mar. 9, 2012

(86) PCT No.: PCT/CN2012/072141
§ 371 (c)(1),
(2), (4) Date: Sep. 9, 2014

(87) PCT Pub. No.: WO2013/131277
PCT Pub. Date: Sep. 12, 2013

(65) Prior Publication Data
US 2015/0044739 A1   Feb. 12, 2015

(51) Int. Cl.
*C12N 1/16* (2006.01)
*C12P 7/44* (2006.01)
*C12R 1/72* (2006.01)

(52) U.S. Cl.
CPC ... *C12N 1/16* (2013.01); *C12P 7/44* (2013.01); *C12R 1/72* (2013.01)

(58) Field of Classification Search
None
See application file for complete search history.

(56) References Cited

U.S. PATENT DOCUMENTS 5,023,347 A * 6/1991 Farbood et al. ............. 549/263
2010/0291653 A1* 11/2010 Ness et al. .................. 435/171

* cited by examiner

*Primary Examiner* — Robert Yamasaki
*Assistant Examiner* — Charles Zoltan Constantine
(74) *Attorney, Agent, or Firm* — Perkins Coie LLP; Yingli Wang

(57) ABSTRACT

A strain of *Candida sake*, CAT H430, is provided. The methods of using CAT H430 for producing dicarboxylic acids are also provided.

6 Claims, 1 Drawing Sheet

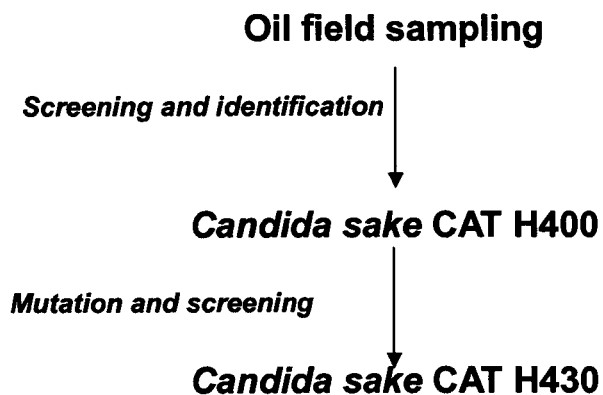

CANDIDA SAKE STRAIN FOR PRODUCING LONG CHAIN DICARBOXYLIC ACIDS

FIELD

The invention relates to a new *Candida sake* strain, CAT H430, and to methods of using CAT H430 for producing dicarboxylic acids, including long chain dicarboxylic acids

BACKGROUND

Long chain diacids ("LCDAs"; also referred to as long chain dicarboxylic acids and long chain dioic acids) include diacids with the formula $HOOC(CH2)_nCOOH$ in which $n \leq 7$. LCDAs are used in the manufacture of a number of products and intermediate products, including polyamides, also known as nylons, used in making electric cable sheathes, tooth brush fibers; adhesive and performance coatings such as those used in co-polyamide adhesives, polyester adhesives, and paints; as GMA powder coat crosslinkers for automobile wheels; as anti-corrosion materials such as metal working fluids and those used in industrial cooling systems; synthetic lubricants, such as automobile lubricants; and in various personal care and household products, such as fragrances and household cleaners.

Chemical synthesis methods for long-chain alpha, omega dicarboxylic acids are available, but the methods are not easy and most of them result in mixtures containing acids having shorter chain lengths. Thus, extensive purification steps are necessary when producing LCDAs using these methods. Several strains of yeast are known to produce LCDAs when cultured on alkanes or fatty acids as the carbon source. There are three biochemical processes by which yeasts metabolize alkanes and fatty acids: α-oxidation of alkanes to alcohols, omega-oxidation of fatty acids to alpha, omega-dicarboxylic acids, and the degradative β-oxidation of fatty acids to $CO2$ and water. Biological conversion processes for the production of diacids have a number of potential advantages over non-biological conversion processes. Primary among these is the option to use renewable feedstocks as starting materials and the ability to produce the diacid without the generation of hazardous chemical byproducts which necessitate costly waste disposal processes. Another important advantage achieved by using a biological process is that such a process can easily be adapted to produce a wide variety of diacids using the same biocatalyst and the same equipment. Because current organic chemical syntheses are suited to the production of only a single diacid, the synthesis of several different diacids would require the development of a new synthetic scheme for each diacid. On the other hand, a yeast biocatalyst can be used to produce diacids of varying lengths using the same equipment, media and protocols merely by providing a different substrate to the yeast.

Despite advances in increasing the yield of dicarboxylic acids obtainable by culturing yeasts such as *Candida tropicalis* strains, there remains a need to provide higher-yielding strains of *Candida* for the production of long chain dicarboxylic acids, including undecanedioic acid, dodecanedioic acid, brassylic acid, tetradecanedioic acid, pentadecanedioic acid, hexadecanedioic acid, and octadecanedioic acid. It is accordingly an object of the invention to provide new strains and methods of using those strains to produce one or more long chain dicarboxylic acids. Using higher yielding strains of *Candida* to produce long chain dicarboxylic acids allows the ordinary artisan to replace the multi-step synthesis used in chemical methods with a higher yielding approach that nevertheless is achieved with low energy consumption and does not require a petrochemical starting material, although such materials may be used in the methods of the invention.

SUMMARY OF THE INVENTION

In accordance with the invention, there is provided a new strain of *Candida sake*, CAT H430, and methods of using CAT H430 to produce dicarboxylic acids.

In some embodiments, CAT H430 may be capable of producing at least 100 g/L of 1,10-Decanedicarboxylic acid in a standard 500 ml shake flask and under the fermentation condition described below. In other embodiments, CAT H430 may be capable of producing at least 100 g/L of 1,10-Decanedicarboxylic acid in a standard 10 L tank and reach over 90% yield (w/w, the weight percentage of alkane converted to dicarboxylic acid) under the fermentation condition described below. In still other embodiments, CAT H430 may be capable of producing at least 100 g/L of 1,10-Decanedicarboxylic acid in a 200 $M^3$ tank and reach over 90% yield (w/w, the weight percentage of alkane converted to dicarboxylic acid) under the fermentation condition described below. In some embodiments, CAT H430 may be capable of producing a dicarboxylic acid with the formula $HOOC(CH2)_n COOH$, in which $n \geq 2$. In some embodiments, the dicarboxylic acid is succinic acid, glutaric acid, adipic acid, pimelic acid, suberic acid, azelaic acid, sebacic acid, undecanedioic acid, dodecanedioic acid, brassylic acid, tetradecanedioic acid, pentadecanedioic acid, hexadecanedioic acid, octadecanedioic acid, or combinations thereof.

In some embodiments, the specification describes a process for producing dicarboxylic acid comprising:

culturing *Candida sake* strain CAT H430 in a medium comprising at least one nitrogen source and at least one organic substrate; and recovering the dicarboxylic acid from the culture.

In some embodiments, the process is one wherein the at least one organic substrate is chosen from: alkanes having from 4 to 22 carbon atoms, carboxylic acids having from 4 to 22 carbon atoms such as fatty acids having from 10 to 22 carbon atoms, and fatty acid alkyl esters formed by esterifying fatty acids having 10 to 22 carbon atoms with alcohols having 1 to 12 carbon atoms. In some embodiments, the process is one in which the dicarboxylic acid is succinic acid, glutaric acid, adipic acid, pimelic acid, suberic acid, azelaic acid, sebacic acid, undecanedioic acid, dodecanedioic acid, brassylic acid, tetradecanedioic acid, pentadecanedioic acid, hexadecanedioic acid, octadecanedioic acid, or combinations thereof.

Additional objects and advantages of the invention will be set forth in part in the description which follows, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 1 illustrates the screening process used in the production of *Candida sake* strain CAT H430.

DESCRIPTION OF THE EMBODIMENTS

Long chain diacids ("LCDAs") include diacids with the formula $HOOC(CH_2)_nCOOH$ in which $n \geq 7$. Examples of LCDA include undecanedioic acid ($HOOC(CH_2)_9COOH$, also known as 1,9-Nonanedicarboxylic acid or 1,11-Undecanedioic acid, and referenced herein as "DC11"), dodecanedioic acid ($HOOC(CH_2)_{10}COOH$, also known as 1,10-Decanedicarboxylic acid or 1,12-Dodecanedioic acid, and referenced herein as "DC12"), brassylic acid ($HOOC(CH_2)_n COOH$, also known as 1,11-Undecanedicarboxylic acid or 1,13-Tridecanedioic acid, and referenced herein as "DC13"), tetradecanedioic acid ($HOOC(CH_2)_2COOH$, also known as 1,12-Dodecanedicarboxylic acid or 1,14-Tetradecanedioic acid, and referenced herein as "DC14"), pentadecanedioic acid ($HOOC(CH_2)_{13}COOH$, also known as 1,15-Pentadecanedioic acid, and referenced herein as "DC15"), hexadecanedioic acid ($HOOC(CH_2)_{14}COOH$, also known as 1,14-Tetradecanedicarboxylic acid, 1,16-Hexadecanedioic acid, or Thapsic acid, and referenced herein as "DC16"), heptadecanedioic acid ($HOOC(CH_2)_{15}COOH$, also known as 1,15-Pentadecanedicarboxylic acid, and referenced herein as "DC17"), and octadecanedioic acid ($HOOC(CH_2)_{16}COOH$, also known as 1,16-Hexadecanedicarboxylic acid, or 1,18-Octadecanedioic acid, and referenced herein as "DC18").

The CAT H430 strain can produce diacids, especially long chain diacids, with various fermentation processes. In some embodiments, the process for producing long chain diacids comprises culturing strain CAT H430 in a medium comprising at least one nitrogen source and at least one organic substrate. In some embodiments, the at least one organic substrate is chosen from alkanes having from 4 to 22 carbon atoms, carboxylic acids having from 4 to 22 carbon atoms (for example, fatty acids having from 10 to 22 carbon atoms) and fatty acid alkyl esters formed by esterifying fatty acids having 10 to 22 carbon atoms with alcohols having 1 to 12 carbon atoms.

The strain CAT H430 provided in the present disclosure was developed from biological samples taken from Shengli oil field in Shandong province in China. Initially, all the collected samples were diluted 1000-fold with 0.7% NaCl solution. The diluted samples were then cultured, and isolated colonies were tested for their abilities to produce long chain diacids. The strains that was capable of producing the highest amount of dicarboxylic acid was named as *Candida sake* CAT H400, and later used as a starting strain for mutagenesis using UV lights and nitrite. CAT H430 is a product of mutagenizing CAT H400.

The CAT H430 strain may be grown in a number of different culture media. One such medium is "YPD Medium," which is an aqueous media comprising 20 g/L glucose, 10 g/L yeast extract, and 20 g/L peptone. The YPD Medium may be prepared with tap water and with 1 N NaOH to adjust the pH to 7.0-7.5. The medium may be sterilized at 121° C. for 20 min. Adding 2% agar by weight to YPD Medium leads to "YPD Agar," which is a gel at room temperature and also suitable for culturing the CAT H430.

Another medium suitable for growing the CAT H430 is "Seed Fermentation Medium," which is an aqueous media comprising: 10-30 g/L sucrose, 1.5-10 g/L corn steep liquor, 1-10 g/L yeast extract, 4-12 g/L KH2PO4, 0.5-5 g/L urea, and 0-30 mL/L dodecane. The medium may be prepared with tap water and sterilized at 121 degrees Celsius for 20 min.

Another medium suitable for growing the CAT H430 is "Fermentation Medium," which is an aqueous media comprising: 1-10 g/L corn steep liquor, 1-10 g/L yeast extract, 5-12 g/L KH2PO4, 0-3 g/L sodium chloride, 4-12 g/L potassium nitrate, 10-40 g/L sucrose, 0.5-3 g/L urea, and 150-300 mL/L n-alkane(s). The medium may be prepared with tap water and with 1 N NaOH to adjust the pH to 7.5-7.8. The medium may be sterilized at 121° C. for 20 min.

Another medium suitable for growth of strain CAT H430 is "Industrial Fermentation Medium," which is an aqueous media comprising: 5-12 g/L KH$_2$PO4, 0-3 g/L MgSO4, 4-12 g/L potassium nitrate, 10-40 g/L, glucose, 0.1-0.5 g/L citric acid, 0.1-0.5 g/L CaCl$_2$ and other metal salts such as ZnSO4, CuSO4 etc. The medium may be prepared with tap water and sterilized at 121° C. for 20 min.

Various fermentation protocols may be used with the CAT H430. In one embodiment, CAT H430 may be used in a "Standard 500 ml Shake Flask Fermentation" comprising:

using an inoculating loop to evenly spread CAT H430, on sterilized YPD Agar in a slant test tube;

culturing CAT H430 at a temperature of 29-30 degrees Celsius for 2 days;

inoculating a portion of the culture (e.g. one third of the slant culture) in 30 ml of sterilized Seed Fermentation Medium in a 500 ml shake flask, which is then incubated for 36-48 hours at a temperature of 29-30 degrees Celsius, a shaker speed of 200-250 rpm, and a shaker amplitude of 2.5-3.5 cm; and removing and inoculating the broth from this seed fermentation into sterilized Fermentation Medium in a 500 ml fermentation flask, which is then incubated for 90-120 hours at a temperature of 29-30 degrees Celsius, a shaker speed 200-240 rpm, a shaker amplitude of 2.5-3.5 cm, and pH between 7.0-8.0 maintained by adding 1 N sodium hydroxide solution when needed. The concentration of dicarboxylic acid in the fermentation broth may be measured after this step.

In another embodiment, the CAT H430 is used with a "10 L Fermentation" protocol comprising:

(1) preparing a CAT H430 seed liquid in a seed tank containing "Seed Fermentation Medium" at 29° C. The seed tank may comprise: a volume of about 10 L, an agitation speed of about 400-500 rpm, an aeration of about 0.2-1.0 M$^3$/h, and a head pressure of about 0.08-0.1 Mpa. The culture time is about 15-24 h.

(2) inoculating the CAT H430 seed liquid to a fermenter containing "Fermentation Medium." The fermenter may comprise: a volume of about 10 L, an agitation speed of about 500-800 rpm, an aeration of about 0.2-1.0 M3/h, and a head pressure of about 0.08-0.1 Mpa. 40% of alkali solution may be used to control the pH of the broth. The pH of the broth is initially at about 6.0-6.4, and then kept at a value higher than about 4-4.5 in the first 18 h. After the first 18 h, the pH is adjusted to and kept at about 7.0-8.0 until the end of the fermentation. The first batch of alkane is added at 15-20 h, when the alkane concentration in the broth is below about 5%. During the fermentation, glucose is added to control β-oxidation. The fermentation time is about 140-180 hrs.

In still another embodiment, the strain CAT H430 is used with a "200 M$^3$ Fermentation" protocol comprising:

(1) preparing a CAT H430 seed liquid in a seed tank containing "Seed Fermentation Medium" at 29° C. The seed tank may comprise: a volume of about 20 M$^3$, an agitator speed of about 100-250 rpm, an aeration of about 0.2-0.5 WM, and a head pressure of about 0.08-0.1 Mpa. The culture time is about 15-24 h; and (2) inoculating the seed liquid to a fermenter containing "Industrial Fermentation Medium." The fermenter may comprise: a volume of about 200 M$^3$, an agitator speed of about 100-150 rpm, an aeration of about 0.2-0.5 WM, and a head pressure of about 0.08-0.1 Mpa. 40% of alkali solution is used to control the pH of the broth. The pH of the broth is initially at about 6.0-6.4, and then kept at a value higher than about 4-5 in the first 18 h. After the first 18 h, the pH is adjusted to and kept at about 7.0-8.0 until the end of the fermentation. The first batch of alkane is added at 15-20 h, when the alkane concentration in the broth is below about 5%. During the fermentation, glucose is added to control β-oxidation. The fermentation time is about 140-180 hrs.

In accordance with the invention, the dicarboxylic acid concentration in the culture medium is determined using techniques known in the art, for example, in Chinese Patent No. ZL95117436.3. Specifically, the fermentation broth may be adjusted to pH 3.0 with hydrochloric acid solution, after which 100 ml of ether is added to extract the diacids. The ether is then evaporated to leave a diacid powder, which is then dissolved in ethanol and titrated with a sodium hydroxide solution of 0.1 mol/L to determine dicarboxylic acid titer in the culture medium.

In some embodiments, the fermentation conditions are those described in detail in the Examples. As a non-limiting example, the fermentation medium may comprise peptone, yeast extract, Yeast Nitrogen Base, potassium dihydrogen phosphate, and sucrose. In some embodiments, the fermentation medium supports the growth of CAT H430 and comprises (a) corn syrup providing a glucose concentration of about 10 to about 60 g/L; (b) an organic nitrogen source selected from the group consisting of corn steep liquor at a concentration of about 1 to about 15 g/L and brewer's yeast extract at a concentration of about 1 to about 10 g/L; (c) a source of inorganic nitrogen; (d) a source of phosphate; (e) optionally a source of trace elements; (f) yeast culture; and (g) a substrate which the yeast can convert to a dicarboxylic acid, such as described in U.S. Pat. No. 6,004,784.

In some embodiments, CAT H430 may produce at least 80%, at least 85%, or at least 90% yield of a dicarboxylic acid. In some embodiments, the dicarboxylic acid produced by CAT H430 is one or more of a undecanedioic acid, a dodecanedioic acid, a brassylic acid, a tetradecanedioic acid, a pentadecanedioic acid, a hexadecanedioic acid, and an octadecanedioic acid. In one embodiment, the dicarboxylic acid produced by CAT H430 is 1,10-Decanedicarboxylic acid.

In some embodiments, CAT H430 may produce at least 95 g/L, at least 100 g/L, at least 110 g/L, at least 120 g/L, at least 130 g/L, at least 140 g/L, at least 150 g/L, or at least 160 g/L of a dicarboxylic acid. In some embodiments, the dicarboxylic acid produced by CAT H430 is one or more of a undecanedioic acid, a dodecanedioic acid, a brassylic acid, a tetradecanedioic acid, a pentadecanedioic acid, a hexadecanedioic acid, and an octadecanedioic acid. In one embodiment, the dicarboxylic acid produced by CAT H430 is 1,10-Decanedicarboxylic acid.

In some embodiments, CAT H430 produces a dicarboxylic acid with the formula $HOOC(CH_2)nCOOH$, in which $6 \geq n \geq 2$. In some embodiments, the dicarboxylic acid is butanedioic acid, pentanedioic acid, hexanedioic acid, heptanedioic acid, octanedioic acid, or combinations thereof In some embodiments, CAT H430 produces a dicarboxylic acid that is a long chain diacid with the formula $HOOC(CH2)nCOOH$, in which $n \geq 7$. In some embodiments, the dicarboxylic acid is nonanedioic acid, decanedioic acid, undecanedioic acid, dodecanedioic acid, brassylic acid, tetradecanedioic acid, pentadecanedioic acid, hexadecanedioic acid, octadecanedioic acid, or combinations thereof.

In some embodiments, a process is described for producing dicarboxylic acid comprising: culturing *Candida sake* strain CAT H430 in a medium comprising at least one nitrogen source and at least one organic substrate; and recovering the dicarboxylic acid from the culture. In some embodiments, the process is one wherein the at least one organic substrate is chosen from: alkanes having from 4 to 22 carbon atoms, carboxylic acids having from 4 to 22 carbon atoms (such as fatty acids having from 10 to 22 carbon atoms), and fatty acid alkyl esters formed by esterifying fatty acids having 10 to 22 carbon atoms with alcohols having 1 to 12 carbon atoms. In some embodiments, the process is one in which the dicarboxylic acid is butanedioic acid, pentanedioic acid, hexanedioic acid, heptanedioic acid, octanedioic acid, nonanedioic acid, decanedioic acid, undecanedioic acid, dodecanedioic acid, brassylic acid, tetradecanedioic acid, pentadecanedioic acid, hexadecanedioic acid, octadecanedioic acid, or combinations thereof.

In certain embodiments, a culture medium is utilized. The various culture media described in the examples provide examples of suitable media that may be used. In general, however, the culture medium can contain any inorganic or organic source of nitrogen normally used in processes for culturing microorganisms. Inorganic nitrogen sources include alkali metal nitrates such sodium or potassium nitrate, ammonium salts such as ammonium sulfate, ammonium chloride, ammonium nitrate, ammonium acetate, and the like. Organic nitrogen sources include urea, corn steep liquor, yeast extracts, and other organic nitrogen sources known to those skilled in the art. The organic substrate can be any aliphatic compound wherein at least one of the terminal carbons is a methyl group and which has at least 9 carbon atoms. Examples of such compounds include alkanes, alkenes, alkynes, carboxylic acids and their esters, and arenes. Examples of suitable substrates are alkanes having from about 9 to about 22 carbon atoms and fatty acids and their alkyl esters wherein the acyl portion contains from about 10 to about 22 carbon atoms. In some embodiments, the substrate is chosen from dodecane, tridecane, tetradecane, oleic acid, methyl oleate, methyl palmitate, methyl palmitoleate or methyl myristate.

Suitable cosubstrates are also described in the examples. Examples of cosubstrates include glucose, fructose, maltose, glycerol and sodium acetate. In some embodiments, the cosubstrate is glucose. A cosubstrate may be used with those strains of *C. sake* in which the beta-oxidation pathway is blocked or inhibited so that energy is not available from the oxidation of the substrate. Glucose added at a definite rate along with the substrate strikes a balance between providing an energy source for the cells while allowing the partial oxidation of the substrate to an alpha, omega-dicarboxylic acid.

The diacids produced using the bio-based methods described above can be used in the manufacture of any product produced using chemically-derived diacids. Some non-limiting examples of products that may be produced using diacids include, but are not limited to, polyamides and nylons, such as those used in making textile fibers; electric cables sheathes or tooth brush fibers; adhesive and performance coatings such as those used in co-polyamide adhesives, polyester adhesives, and paints; as GMA powder coat crosslinkers for automobile wheels; anti-corrosion materials such as metal working fluids and those used in industrial cooling systems; synthetic lubricants, such as automobile lubricants; and in various personal care and household products, such as fragrances and household cleaners.

Both the foregoing general description and the following detailed description are exemplary and explanatory only and are not restrictive of the invention, as claimed. Moreover, the invention is not limited to the particular embodiments described, as such may, of course, vary. Further, the terminology used to describe particular embodiments is not intended to be limiting, since the scope of the present invention will be limited only by its claims.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference.

It must be noted that, as used herein and in the appended claims, the singular forms "a," "or," and "the" include plural referents unless the context clearly dictates otherwise. Further, all numbers expressing quantities of ingredients, reaction conditions, % purity, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

The following examples further illustrate the invention. They are merely illustrative of the invention and disclose various beneficial properties of certain embodiments of the invention. The following examples should not be construed as limiting the invention.

EXAMPLES

Example 1

Screening Procedures for the CAT H430 Strain

The strain CAT H430 was produced by mutagenesis of strain CAT H400, which is an isolate obtained from samples taken from Shengli oil field in Shandong province in China. Initially, samples taken from Shengli oil field in Shandong province in China were diluted 1000 times with 0.7% NaCl solution and then inoculated to plates containing YPD medium. All of the samples were cultured at 28-30° C. Separated colonies grown on the plates were removed and then inoculated into standard 500 ml Shake Flask Fermentation to screen for isolates that produce the highest amount of dicarboxylic acid. One strain that produced 10 g/L dicarboxylic acid was separated and named as CAT H400. It is the strain selected for subsequent characterization and mutagenesis.

Example 2

Characteristics of the CAT H400 Strain

Morphology (colony on potato dextrose agar): cream-colored, butyrous. Blastospores ellipsoidal-ovoid, pseudomycelium and true mycelium present. No sexual propagation detected.

Utiliization of C- and N-Source

| anaerobic | Glucose | + | | |
|---|---|---|---|---|
| aerobic | Glucose | + | a-methylglycoside | + |
| | Galactose | + | Salicin | + |
| | Sorbose | − | Cellobiose | + |
| | Rhamnose | − | Maltose | + |
| | Dulcit | − | Lactose | − |
| | Inositol | − | Melibiose | − |
| | Manitol | + | Sucrose | + |
| | Sorbitol | + | Trehalose | + |
| | Glycerol | + | Inulin | − |
| | Erythritol | − | Metezitose | − |
| | D-Arabinose | − | Raffinose | − |
| | L-Arbinose | − | Starch | − |
| | Ribose | − | Xylitol | − |
| | D-Xylose | + | Gluconate | + |
| | L-Xylose | − | 2-keto-Gluconate | + |
| | Adonitol | + | 5-keto-Gluconate | + |
| | Nitrate | − | | |

Additional tests:
Growth with N-acetylglucosamine (+)
Growth at 37° C. (−)
Urease (−)
Identification:
CAT H400 is a strain of *Candida sake*.

Example 3

Mutagenesis and Screening Procedures for CAT H430 Strain

Diacid producing cultures of strain CAT H400 were separated and purified, and preserved in a glycerol tube in a low-temperature refrigerator until use. One tube of the glycerol preserved strains was thawed at room temperature, then inoculated into a 500 ml Erlenmeyer flask with 50 ml liquid YPD Medium and cultured in a rotary shaker at 210 rpm at 29° C. for 20-24 hrs.

To prepare the strain suspension for mutagenesis, 10 ml of YPD Medium was added to a 15 ml sterile centrifuge tube, centrifuged at 2000 rpm for 2 minutes, and the supernatant discarded. The pellet was washed 3 times using 0.85% saline and centrifugation. After the washing, the supernatant was discarded and 10 ml of 2.5% sterile lithium chloride was added to prepare the strain suspension.

To prepare the N-methyl-N'-nitro-N-nitrosoguanidine ("NTG") mutagen, 0.08 mg of NTG mutagen was weighed out and added into a 15 ml sterile centrifuge tube to which 10 ml of 0.85% saline was then added and the contents mixed.

10 ml of the lithium chloride strain suspension and 10 ml of the NTG solution were mixed and placed into a 90 mm sterile petri dish with a 15 mm by 3 mm stirrer, and the top covered. Two additional dishes were prepared by the same method. The three dishes were then stirred on a magnetic stirrer for 10, 15, and 20 minutes, respectively.

Each of the dishes were then processed. In brief, 10 ml of the above treated solution was transferred into a 15 ml sterile centrifuge tube, centrifuged at 2000 rpm for 2 minutes, the supernatant discarded, and the pellet washed 3 times using 0.85% saline.

After the final wash, the supernatant was discarded and the pellet diluted stepwise with 0.85% saline. 0.15 ml of each dilution was spread over plates with YPD agar medium, which were then cultured in an inverted position in an incubator at 29° C. for 3-4 days.

Following culture, mature single colonies were picked from the plates, inoculated into a 15 by 150 mm test tube slant, and cultured in a incubator at 29° C. for 2 days to form a slant culture.

After two days of incubation, one third of the slant culture was removed, inoculated into a 250 ml Erlenmeyer flask with 10 ml Fermentation Medium and cultured in a rotary shaker at 210 rpm at 29° C. for 4 days. The remaining slant culture was stored in a refrigerator at 4° C. At the same time, 6 flasks of control strains were transferred into each layer of the shaker, uniformly distributed in 6 positions of the shaker.

At the end of the fermentation step, 0.05 ml of 1% phenolphthalein was added into each flask of fermentation broth using a pipette gun. Ten flasks of fermentation broth were selected either randomly or because they were growing well. The 6 flasks of control strains were also selected, resulting in a total of 16 flasks that were further processed.

The weight of these 16 fermentation flasks was taken and recorded, then the flasks were titrated with 0.2 N alkali solution. After the titration end point was reached, the fermentation flasks were weighed again and the weight recorded.

The average shake-flask alkali consumption of the control strains and alkali consumption of the screened strains was then calculated and the level of alkali consumption of the screened strains determined. Typically in this preliminary screening the alkali consumption of the screened strains increased by 10% or more compared to the control strains.

0.2 N alkaline solution and 0.05 ml of a 1% phenolphthalein solution was added into control strain flasks to determine how much alkali was required for the neutralization reaction. This amount of alkali and 0.05 ml phenolphthalein (1%) were added to other shake flasks. Flasks that turned red indicated mutant strains producing less acid then the control one. The flasks were then shaken for 5 minutes. After the 5 minutes, the flasks were checked for any color changes and all of the discolored flasks were removed. Titration was continued for those flasks that did not discolor, and they were finally weighed and the alkali consumption calculated.

The strains to be rescreened were determined based on the alkali consumption of the fermentation shake flasks. Generally, of the 100 strains produced from the preliminary screening, the five strains that consumed the highest amount of alkali were selected for rescreening.

For rescreening, one fifth of the remaining slant (i.e., two thirds of the original slant set aside during the preliminary screening) was transferred to slant F2 for culture in a incubator at 29° C. for 2 days. The remaining slants were returned to storage in a refrigerator.

Following the initial slant culture period, the whole tube of mature slant thalli was transferred into a 500 ml Erlenmeyer flask with 30 ml seed medium which was then cultured in a rotary shaker at 210 rpm at 29° C. for 44-48 hrs. One whole tube of glycerol broth of the control strain was also inoculated into a seed shake flask with Seed Fermentation Medium.

From the mature seed solution, 3 ml was removed and add into a 500 ml Erlenmeyer flask with 15 ml Fermentation Medium. The culture was incubated in a rotary shaker at 210 rpm at 29° C. for 110 hr.

The resulting strain CAT H430 was obtained after the screening procedure was repeated multiple times.

Example 4

Production of LCDAs Using CAT H430 in a 500 ml Shake Slask

The average titers for dodecanedioic acid (DC12), brassylic acid (DC13), and DC14 produced by strain CAT H430 in 500 ml shake flasks and under the fermentation conditions described above are presented in Table 1.

TABLE 1

| Strain ID | Raw material | Titre (g/L) | Product |
| --- | --- | --- | --- |
| CAT H430 | C12 | 152.09 | DC12 |
|  | C13 | 103.08 | DC13 |
|  | C14 | 150.54 | DC14 |
|  | C14 fame | 110.42 | DC14 |
| CAT H400 | C12 | 15 | DC12 |

Example 5

Production of LCDAs Using CAT H430 in a 10 L Fermentor

The average titres for dodecanedioic acid (DC12)) and brassylic acid (DC13) produced by strain CAT H430 in 10 L fermentors and under the fermentation conditions described above are presented in Table 2 and Table3.

TABLE 2

| 10 L Tank NO | 1# | 2# | 3# | 4# | 5# | 6# |
| --- | --- | --- | --- | --- | --- | --- |
| Fermentation time (h) | 166 | 166 | 166 | 166 | 166 | 150 |
| DC12 titre (mg/g) | 129.58 | 131.61 | 119.57 | 125.53 | 142.71 | 134.8 |
| yield | 84.75% | 90.62% | 96.02% | 97.26% | 90.74% | 90.49% |

TABLE 3

|  | 10 L Tank NO | |
| --- | --- | --- |
|  | 3# | 12# |
| Fermentation time (h) | 166 | 146 |
| DC13 titre (mg/g) | 121.4 | 131 |
| yield | 92.3% | 6.2% |

Example 6

Production of LCDAs Using CAT H430 in a 200 $M^3$ Fermentor

The average titres for dodecanedioic acid (DC12) produced by strain CAT H430 under the fermentation conditions described above, is presented in Table 4.

TABLE 4

|  | 200$M^3$ Tank Batch NO | | |
| --- | --- | --- | --- |
|  | 301#-282-01 | 307#-299-06 | 307#-292-03 |
| Fermentation time (h) | 188 h | 131 | 172 |
| DC12 titre (mg/g) | 135.1 | 143.7 | 148.1 |
| yield | 87.7% | 90.76% | 94.57% |

CAT H430 produced higher titers of dodecanedioic and brassylic acids than *Candida sake* strains previously reported in the literature.

Biological Deposit Information:

*Candida sake* strain CAT H430 was deposited in accordance with the Budapest Treaty on Dec. 29, 2011, with the China Center for Type Culture Collection (CCTCC), Wuhan University, Wuhan 430072, China. The deposit was given accession number M2011489.

What is claimed is:

1. *Candida sake* strain CAT H430 with CCTCC No. M2011489.

2. A process for producing dicarboxylic acid comprising:
culturing *Candida sake* strain CAT H430 with CCTCC No. M2011489 in a medium comprising at least one nitrogen source and at least one organic substrate; and
recovering the dicarboxylic acid from the culture.

3. The process according to claim 2, wherein the at least one organic substrate is chosen from alkanes having from 9 to 22 carbon atoms, carboxylic acids having from 9 to 22 carbon atoms, or fatty acid alkyl esters formed by esterifying fatty acids having 10 to 22 carbon atoms with alcohols having 1 to 12 carbon atoms.

4. The process according to claim 2, wherein the dicarboxylic acid is undecanedioic acid, dodecanedioic acid, brassylic acid, tetradecanedioic acid, pentadecanedioic acid, hexadecanedioic acid, octadecanedioic acid, or combinations thereof.

5. A composition comprising *Candida sake* strain CAT H430 with CCTCC No. M2011489, at least one nitrogen source, and at least one organic substrate.

6. A composition comprising *Candida sake* strain CAT H430 with CCTCC No. M2011489 and at least one dicarboxylic acid, wherein the dicarboxylic acid is undecanedioic acid, dodecanedioic acid, brassylic acid, tetradecanedioic acid, pentadecanedioic acid, hexadecanedioic acid, octadecanedioic acid, or combinations thereof.

* * * * *